United States Patent [19]
Schiller et al.

[11] Patent Number: 5,786,447
[45] Date of Patent: Jul. 28, 1998

[54] OPIOID PEPTIDE ANALOGS

[75] Inventors: Peter Schiller; Ralf Schmidt, both of Montreal, Canada

[73] Assignee: Astra AB, Sweden

[21] Appl. No.: 448,472

[22] PCT Filed: Apr. 27, 1995

[86] PCT No.: PCT/SE95/00462

§ 371 Date: May 31, 1995

§ 102(e) Date: May 31, 1995

[87] PCT Pub. No.: WO95/30694

PCT Pub. Date: Nov. 16, 1995

[30] Foreign Application Priority Data

May 6, 1994 [SE] Sweden ............... 9401596

[51] Int. Cl.$^6$ ........................ C07K 7/00
[52] U.S. Cl. ............ 530/317; 530/330; 530/334; 530/342; 514/9; 514/11; 514/17
[58] Field of Search ............... 514/9, 11, 17; 530/317, 330, 334, 342

[56] References Cited

U.S. PATENT DOCUMENTS 4,707,468  11/1987  Yoshino et al. ............... 514/16

OTHER PUBLICATIONS

Derwent's abstract, No. 90-42476/06, week 906, Abstract of SU 1095-587-A (As Latv. Org. Synthesis) (30 Aug. 1989).
Abelhamid et al., "Selective Blockage of Delta Opioid Receptors Prevents the Development of Morphine Tolerance and Dependance in Mice," *J. Pharmacol. Exp. Ther.* 258: 299-303 (1991).
Schiller et al., "Differential Stereochemical Requirements of μ vs. δ Opioid Receptors for Ligand Binding and Signal Transduction: Development of a Class of Potent and Highly δ-Selective Peptide Antagonists," *Proc. Natl. Acad. Sci. USA* 89:11871-11875 (1992).
Schiller et al., "Conformationally Restricted Deltorphin Analogues," *J. Med. Chem.* 35: 3956-3961 (1992).
Schmidt, et al., *J. Med. Chem.*, 37, 1136-1144, 1994.
Schmidt et al., *Int. J. Peptide Protein Res.*, 37, 502-507, 1991.
STN Fastnotes from STN International.

*Primary Examiner*—Cecilia J. Tsang
*Assistant Examiner*—C. Delacroix-Muirheid
*Attorney, Agent, or Firm*—Michael A. Sanzo; Vinson & Elkins

[57] ABSTRACT

Compounds of the formula I as well as methods for their preparation, their pharmaceutical preparations and their use as analgesics.

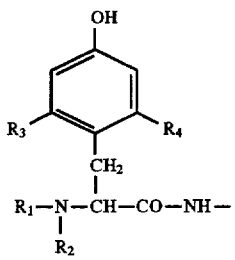

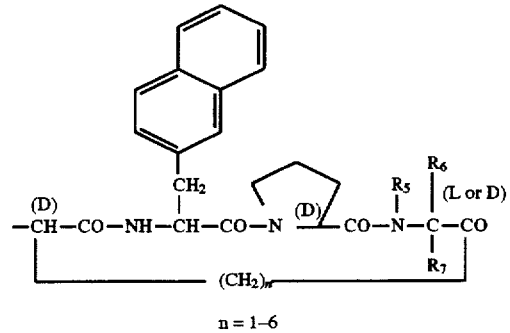

n = 1-6

14 Claims, No Drawings

OPIOID PEPTIDE ANALOGS

CROSS REFERENCE TO RELATED APPLICATIONS

This application is a continuation of international application PCT/SE95/00462, having an international filing date of Apr. 27,1995, and claiming priority to national application 94 01 596-3, filed in Sweden on May 6, 1994.

THE FIELD OF THE INVENTION

This invention is related to a new class of opioid peptide analogs with mixed μ agonist/δ antagonist properties as well as to their synthesis and their use as analgesic compounds.

BACKGROUND

The results of a recent study by E. E. Abdelhamid et al., J. Pharmacol. Exp. Ther. 258, 299–303 (1991), indicated that concurrent chronic administration of morphine and the non-peptide δ antagonist naltrindole attenuated the development of morphine tolerance and dependence. This important observation suggested that a mixed μ agonist/δ antagonist may be therapeutically useful as analgesic with low propensity to produce tolerance and dependence. Thus, for therapeutic applications the availability of such a single compound with mixed μ agonist/δ antagonist properties would be preferable to a combination of a μ-agonist (e.g. morphine) and a δ antagonist, i.e. a mixture of two compounds.

The first known mixed μ agonist/δ antagonist was the tetrapeptide amide H-Tyr-Tic-Phe-Phe-NH$_2$(TIPP-NH$_2$; Tic=1,2,3,4-tetrahydroisoquinoline-3-carboxylic acid) described by P. W. Schiller et al. Proc. Natl. Acad. Sci. USA 89, 11871–11875 (1992). Whereas TIPP-NH$_2$ has a strong δ antagonist component and a relatively weaker μ agonist component, its analogs containing a Dmt (2',6'-dimethyltyrosine) residue in place of Tyr$^1$ show potent μ agonist and very potent δ antagonist opioid effects.

Prior art

Cyclic β-casomorphin analogs with mixed μ agonist/δ antagonist properties have recently been disclosed by R. Schmidt et al. at the 13th American Peptide Symposium, Edmonton, Canada, Jun. 20–25, 1993, and at the 3rd International Symposium on β-Casomorphins and Related Peptides, Skövde, Sweden, Jul. 15, 1993. These compounds show a strong μ agonist component but a relatively weak δ antagonist component. Thus the problem with the compounds known from prior art is that they do not show both a strong μ agonist activity and a strong δ antagonist activity.

THE INVENTION

It has now unexpectedly been found that the compounds of the following formula I have very high μ opioid agonist potency high δ opioid antagonist potency and thus represent a novel class of mixed μ agonist/δ antagonists. Similar to [Dmt$^1$]TIPP-NH$_2$ and its analogs, these compounds show very potent μ agonist potency and very potent δ antagonist potency.

The compounds according to the present invention have the formula I

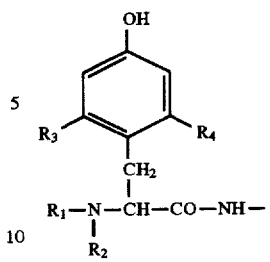

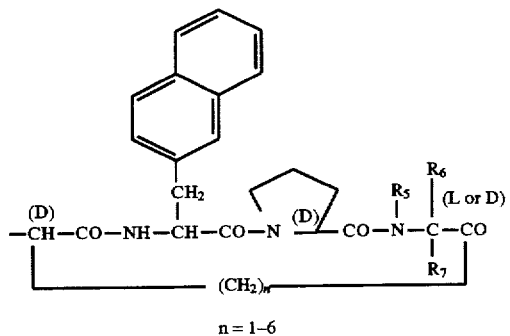

n = 1–6 wherein R$_1$ is H, CH$_3$(CH$_2$)$_n$— wherein n=0–12—, preferably n=0–5,

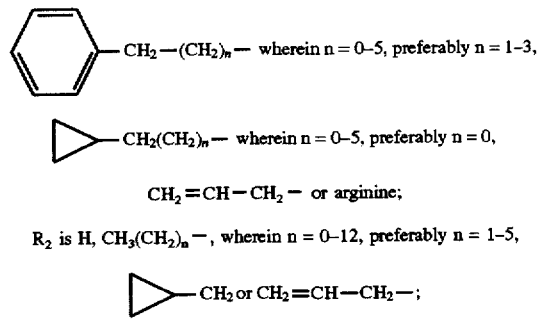

R$_3$ and R$_4$ respectively are both H or are both C$_1$–C$_6$ alkyl groups, preferably a C$_1$–C$_4$ alkyl group;

R$_5$ is H or a C$_1$–C$_6$ alkyl group, preferably a C$_1$–C$_4$ alkyl group;

R$_6$ is H or a C$_1$–C$_6$ alkyl group, preferably a C$_1$–C$_4$ alkyl group;

R$_7$ is H or a C$_1$–C$_6$ alkyl group, preferably a C$_1$–C$_4$ alkyl group; with the exceptions of compounds wherein R$_1$, R$_2$, R$_3$, R$_4$, R$_5$, R$_6$ and R$_7$ are all H, and the number (n) of methylene groups in the 2-position side chain is 2, 3 or 4.

Especially preferred compounds according to the invention are those wherein R$_3$ and R$_4$ are CH$_3$. Introduction of methyl substituents at the 2'-and 6'positions of the Tyr$^1$ aromatic ring drastically increases both μ agonist potency and δ antagonist potency.

Preferred compounds according to the invention are compounds of the

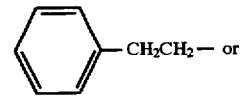

-continued

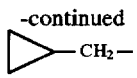

R$_2$ is hydrogen;
R$_3$ and R$_4$ are each a CH$_3$ group;
R$_5$ is hydrogen;
R$_6$ is CH$_3$; and R$_7$ is hydrogen.

The most preferred compounds known at present are the compounds according to Examples 3 and 10.

SYNTHESIS

General Methods

Melting points were determined on a micro hot plate according to BOETIUS and are uncorrected. Optical rotations were measured with a JASCO DIP-370 digital polarimeter. Boc-amino acids were purchased from Bachem Bioscience. Solvents for the synthesis were of analytical grade and were used without further purification with the exception of DMF, which was distilled from ninhydrin and stored under n$_2$. TLC was performed on precoated silica gel plates 60F-254 (E. Merck, Darmstadt, FRG) in the following solvent systems (all v/v):

(A) chloroform/MeOH (9:1),
(B) benzene/acetone/AcOH (25:10:0.5),
(C) ethyl acetate/pyridine/AcOH/H$_2$ (90:15:4.5:8.3);
(D) 2-BuOH/HCOOH/H$_2$O(75/15/20),
(E) 1-BuOH/AcOH/ethyl acetate/H$_2$O(1/1/1/1) and
(F) 1-BuOH/pyridine/AcOH/H$_2$O(15/10/3/12).

Peptides were visualized with UV, the ninhydrin spray reagent and KI/starch. The HPLC system GOLD (Beckman) consisting of a programmable solvent module 126 and a diode array detector module 168 was used for the purification and the purity control of the peptides. Recording and quantification were accomplished using the GOLD software. A LiChrospher 100 RP-18e column (250×4 mm, 5 µm particle size) and a Vydac 218TP54 column were used for all analytical applications. The solvents were of HPLC grade and were filtered and degassed prior to use. HPLC was carried out using a gradient made up from two solvents:

(A) 0.1% TFA in water,
(B) 0.1% TFA in acetonitrile.

The analytical determinations were performed with a linear gradient of 20–50% of (B) over a period of 25 min with a flow rate of 1.5 mL/min in the case of the Merck column (HPLC system I) and of 1 mL/min in the case of the Vydac column (HPLC system Ia), absorptions being measured at both 216 nm and 280 nm. The cyclization reaction was monitored by using the following HPLC conditions: linear gradient 30–80% B over 25 min, detection at 216 nm and 280 nm, flow rate 1.5 mL/min (LiCrospher 100 RP-18e column, HPLC solvent system II) and a flow rate of 1 mL/min (Vydac 218TP54 column, HPLC system IIa).

Molecular weights of the peptides were determined by FAB mass spectrometry on an MS-50 HMTCTA mass spectrometer and by Ionspray mass spectrometry on an SCIEX API III mass spectrometer.

Proton NMR spectra of the purified peptides were recorded in DMSO-d$_6$ solution at 308 K on a VARIAN VXR-400S spectrometer equipped with a Sun workstation. For the recording of proton spectra nondegassed samples in 5 mm tubes were used. Resonance assignments were made by analysis of the 1-D $^1$H and 2-D H,H-COSY spectra.

Peptide Synthesis. Mixed Anhydride Method (A).

NMM (1 equiv.) was added to a stirred solution of the Boc-protected amino acid in THF. The mixture was cooled to −15° C., treated with IBCF (1 equiv.), and allowed to react for 3–4 min. Subsequently, the amino component in the form of the peptide hydrochloride (1 equiv.) was added, followed by NMM (1 equiv.). Stirring proceeded for 30 min at −15° C., and then the mixture was allowed to reach RT. The solvent was removed in vacuo and the residual oil was dissolved in 150 mL EtOAc. The resulting solution was extracted consecutively with brine, 5% KHSO$_4$, brine, saturated NaHCO$_3$, and brine. The organic phase was dried (MgSO$_4$), filtered and evaporated to dryness. The residue was crystallized from appropriate solvents.

Deprotection Procedures. Method B

The Boc-protected peptide was treated with 1.1 N HCl/AcOH (3 equiv.) for 30 min at room temperature. The solvent was evaporated in vacuo at 20° C. and the residue was precipitated with dry ethyl ether. Crude products were crystallized from EtOH/ether or EtOH/DIPE.

The invention will now be described in more detail by way of the following examples, which are not to be construed as limiting the invention.

EXAMPLES

Example 1

Preparation of Tyr(NMe)-cydo[-D-rn-2-Nal-D-Pro-Gly-]
Boc-D-Pro-Gly-ONb (1)

Boc-D-Pro-OH (20 mmol) was reacted with H-Gly-ONb*HCl according to method A, yielding compound 1 after crystallization from DIPE (94%): mp 96–98° C.; $[\alpha]_D^{20}$+51.0° C.(c 1.0, AcOH); TLC R$_f$A 0.65, R$_f$B 0.45, R$_f$C 0.93.

Boc-2-Nal-D-Pro-Gly-ONb (2).

According to method A, Boc-2-Nal-OH (3mmol) was reacted with H-D-Pro-Gly-ONb*HCl (obtained from 1 after treatment as described in method B). Crude 2 was crystallized from EtOAc/DIPE (75%): mp 93–95° C.; $[\alpha]_D^{20}$+ 36.8° C. (c 1.0, MeOH); TLC R$_f$A 0.65, R$_f$B 0.35, R$_f$C 0.84.

Boc-D-Orn(Z)-2-Nal-D-Pro-Gly-ONb (3)

As described in method A, Boc-D-Orn(Z)-OH (0.93 mmol) was reacted with H-2-Nal-D-Pro-Gly-ONb*HCl (obtained from 2 by using deprotection procedure B), yielding 3 after crystallization from DIPE (80%): mp 74–76° C.$[\alpha]^{D20}$+31.9° C. (c 1.0, MEOH); TLC R$_f$A 0.50, R$_f$B 0.26, R$_f$C 0.91.

Boc-Tyr(NMe,Bzl)D-Orn(Z)-2-Nal-D-Pro-Gly-ONb (4).

Boc-Tyr(NMe,Bzl)-OH (0.59 mmol) and H-D-Orn(Z)-2Nal-D-Pro-Gly-ONb*HCl obtained from 3 by deprotection using method B, were coupled (method A) to yield 4 after crystallization from DIPE (85%): mp 80–82° C.; $[\alpha]D^{20}$+ 21.3° C.(c 1.0, MeOH); TLC R$_f$A 0.71, R$_f$B 0.35, R$_f$C 0.90.

Boc-Tyr(NMe)-D-Orn-2-Nal-D-Pro-Gly-OH (5)

The protected peptide 4 (0.23 mmol) was dissolved in 20 mL aqueous MeOH, and the hydrogenation was carried out under atmospheric pressure and at room temperature in the presence of Pd black with a peptide to catalyst ratio of 3:1. After complete removal of the benzyl type protecting groups as monitored by TLC, the solution was filtered, the filtrate was concentrated in vacuo and the residue was crystallized from EtOH/ether, yielding compound 5 (74%): mp 170–172° C.;$[\alpha]D^{20}$+34.3° C.(c 1.0, MeOH); TLC R$_f$E 0.67, R$_f$F 0.64; k' (HPLC system II) 4.51, k' (HPLC system IIa) 2.14.

Boc-Tyr(NMe)-c[-D-Orn-2-Nal-D-Pro-Gly-] (6)

The linear precursor peptide 5 (0.146 mmol) dissolved in 20 mL DMF was added to a cold solution (−25° C.) of DMF (final peptide concentration 1 mM) containing NMM (1 equiv.) and DPPA (2 equiv.). The solution was continously stirred at −25° C. and progress of the reaction was monitored by HPLC (see General Methods). Every 24 h additional NMM and DPPA (1 equiv.) were added and the reaction was allowed to continue until peptidic starting material could no longer be detected. The solvent was then removed under reduced pressure (bath temperature 25° C.) and the obtained residue was triturated 3 times with PE. The residual oil was dissolved in ETOH and precipitated with 5% KHSO$_4$ solution. After filtration and washing with water, the solid was dried in vacuo followed by recrystallization from EtOAc-DIPE, yielding the cyclic peptide 6 (78%): mp 186–188° C.; [α]D$^{20}$ –26.2° C.(c 1.0, MeOH); k' (HPLC system II) 6.88 (95% purity), k' (HPLC system IIa) 4.18 (96% purity); FAB-MS MH$^+$743.

Tyr(NMe)-c[-DOrn-2-Nal-D-Pro-Gly-] (7)

The Boc-protected cyclic peptide 6 (0.092 mmol) was deprotected using aqueous 95% TFA containing thioanisole (3%) under stirring and ice cooling. After evaporation in vacuo, the peptide TFA salt was obtained by precipitation with dry ether (90%). The crude product was purified by preparative RP-HPLC (see General Procedure) on a Vydac 218TP1022 column under isocratic conditions, eluent 0.1% TFA in water/0.1% TFA in acetonitrile (77:23), flow 12/min, detection 215 and 280 nm. The following analytical data were obtained for the final product 7: TLC R$_f$E 0.67, R$_{fi\,F}$ 0.64, k' (HPLC system I) 5.61 (97% purity), k' (HPLC system Ia) 3.23 (97% purity); FAB-MS MH+643, Ion spray (m/z) 643.5.

$^1$H-NMR (δ in ppm): Tyr: NH 8.85, αH 3.78, βH 2.71, 3.02, H$_{aromat}$ 6.73, 6.97, OH 9.44, NMe 1.99; D-Orn: αNH 7.94, δNH 6.55, αH 4.17, βH 1.01, 1.22, γH 1.3, δH 2.71, 3.26; 2-Nal: NH 7.91, αH 4.58 βH 3.09, 3.22, H$_{aromat}$ 7.4–7.9; D-Pro: αH 4.11, βH 1.82, γH 1.49, 1.72, δH 3.12, 3.75; Gly: NH 7.58, αH 3.4, 3.89.

Example 2

Preparation of H-Tyr-c[-D-Orn-2-Nal-D-Pro-Sar-]

The title compound was prepared by peptide synthesis, solid-phase method.

All protected amino acids derivatives were purchased from Bachem Bioscience, Philadelphia, Pa. All solvents were of analytical grade and were used without further purification. Peptide synthesis was performed by the manual solid-phase technique using 0.3 g FMOC-Sar-Sasrin resin® (substitution 0.7 mmol/g resin) obtained from BACHEM Bioscience Philadelphia, Pa. The α-amino group was deprotected by treatment with 20% piperidine in DMF (1×3 min, 1×7 min). After deprotection the resin was alternately washed with DMF and CH$_2$Cl$_2$ (4×2 min each). Fmoc-2-Nal-D-Pro-OH was obtained by coupling Fmoc-2-Nal-OH with H-D-Pro-OtBu using the mixed anhydride method and subsequent treatment with 95% TFA. 0.28 g (0.525 mmol) of the N-protected dipeptide was coupled to the H-Sar-Sasrin-resin using 0.525 mmol diisopropylcarbodiimide (DIC) and 0.1 equiv. 4-dimethylaminopyridine (DMAP). Fmoc-D-Orn(Boc)-OH and Fmoc-Tyr-OH (0.525 mmol each) were coupled using DIC (0.525 mmol) and 1-hydroxybenzotriazole (HOBt) as coupling reagent.

The following steps were performed for each cycle: (1) addition of Fmoc-amino acid (2.5 equiv.) in DMF, (2) addition of HOBt (2.5 equiv.) and mixing for 1 min, (3) addition of DIC (2.5 equiv.) and mixing for 2–3 h, (4) washing alternately with DMF and CH$_2$Cl$_2$ (3×2 min each), (5) washing with EtOH (2 min), (6) monitoring completion of the reaction with the KAISER test, (7) Fmoc deprotection with 20% (v/v) piperidine in DMF (1×3 min, 1×7 min), (8) washing alternately with DMF and CH$_2$Cl$_2$ (4×2 min each). After coupling of the N-terminal Fmoc-Tyr-OH, the resin was alternately washed with DMF and CH$_2$Cl$_2$ (3×2 min each), followed by washing with MeOH and subsequent drying of the resin in vacuo. The partially protected peptide Fmoc-Tyr-D-Orn(Boc)-2-Nal-D-Pro-Sar-OH was obtained by extraction of the peptide resin with 50 ml 1% TFA in CH$_2$Cl$_2$ (3×15 min). After neutralization of the acidic CH$_2$Cl$_2$ solution with pyridine, the solvent was evaporated in vacuo and the residual oil was precipitated from CH$_2$Cl$_2$ with dry ether, yielding 0.1 g (0.1 mmol) of crude Fmoc-Tyr-D-Orn(Boc)-2-Nal-D-Pro-Sar-OH. The N$^δ$-Boc group was removed by treatment with 1N HCl/AcOH and the resulting crude cyclization precursor (0.095 g=0.1 mmol) was used without further purification. The cyclization reaction and the isolation of the cyclic peptide Fmoc-Tyr-c[-D-Orn-2-Nal-D-Pro-Sar-] were performed as described for compound 6 (see above), yielding 0.075 g (0.086 mmol) of crude Fmoc-Tyr-c[-D-Orn-2-Nal-D-Pro-Sar-]. The Fmoc-group was removed by treatment with 10% diethylamine in DMF at roomtemperature (1 h), the solvent was removed in vacuo and the crude product 8 was isolated after precipitation with dry ethyl ether.

Purification was achieved using preparative RP-HPLC (see General Procedure) on a Vydac 218TP1022 column under isocratic conditions (eluent 0.1% TFA/0.1% TFA in acetonitrile (77:23), flow rate 12 mL/min, detection at 215 and 280 nm). The following analytical data were obtained for the final product H-Tyr-c[-D-Orn-2-Nal-D-Pro-Sar-] (8): TLC R$_{71}$ E 0.63, k' (HPLC system I) 6.08 (97% purity), k' (HPLC system Ia) 4.45 (97% purity); FAB-MH$^+$643, Ion spray (m/z) 643.50.

The compounds according to Examples 3–9 were prepared as described for the compounds of Examples 1 and 2 respectively. In Table A below the mode of preparation for the compounds of each Example is indicated.

The following compounds according to the invention have been synthesized. The results are shown in Table A. The method of synthesis is indicated with SS (solution synthesis) or SP (solid phase synthesis).

TABLE A

| Ex. | Compound | Method of synthesis | FAB-MS MH+ |
|---|---|---|---|
| 1 | Tyr(NMe)-c[-D-Orn-2-Nal-D-Pro-Gly-] | SS | 646 |
| 2 | H-Tyr-c[-D-Orn-2-Nal-D-Pro-Sar-] | SP | 645 |
| 3 | H-Dmt-c[-D-Orn-2-Nal-D-Pro-Gly-] | SS | 659 |
| 4 | H-Dmt-c[-D-Orn-2-Nal-D-Pro-Sar-] | SP | 673 |
| 5 | H-Tyr-c[-D-Orn-2-Nal-D-Pro-D-Ala-] | SP | 645 |
| 6 | H-Tyr-c[-D-Orn-2-Nal-D-Pro-Aib-] | SS | 659 |
| 7 | H-Tyr-c[-D-Orn-2-Nal-D-Pro-MeAib-] | SS | 673 |
| 8 | H-Tyr-c[-D-Orn-2-Nal-D-Pro-D-Val-] | SS | 673 |
| 9 | H-Tyr-c[-D-Orn-2-Nal-D-Pro-D-Ile-] | SS | 687 |
| 10 | H-Dmt-c[-D-Orn-2-Nal-D-Pro-D-Ala-] | SS | 673 |

SS = solution synthesis; SP = solid-phase synthesis

Pharmacological testing in vitro of mixed μ agonist/δ antagonists

The compounds shown in Tables 1–3 have been tested in opioid receptor binding assays and biossays.

a) Bioassays based on inhibition of electrically evoked contractions of the mouse vas deferens (MVD) and of the guinea pig ileum (GPI). In the GPI assay the opioid effect is primarily mediated by μ opioid receptors, whereas in the MVD assay the inhibition of the contractions is mostly due to interaction with δ opioid receptors. Antagonist potencies in these assays are expressed as so-called K$_e$-values (H. W. Kosterlitz & A. J. Watt, Br. J. Pharmacol. 33, 266–276 (1968). Agonist potencies are expressed as IC50 values (concentration of the agonist that produces 50% inhibition of the electrically induced contractions).

Bioassays Using Isolated Organ Preparations

The GPI and MVD bioassays were carried out as reported in P. W. Schiller et al., Biochem. Biophys. Res. Commun 85, 1332–1338 (1978) and J. Di Maio et al., J. Med. Chem. 25, 1432–1438 (1982). A log dose-response curve was determined with [Leu⁵] enkephalin as standard for each ileum and vas preparation, and IC50 values of the compounds being tested were normalized according to A. A. Waterfield et al., Eur. J. Pharmacol. 58, 11–18 (1979). $K_e$ values for the cyclic β-casomorphin analogs with mixed μ agonist/δ antagonist properties (δ antagonist effect) were determined from the ratio of IC50 values (DR) obtained in the presence and absence of a fixed antagonist concentration (a) ($K_e$=a/(DR-1)) H. W. Kosterlitz & A. J. Watt, Br. J. Pharmacol. 33, 266–276 (1968). These determinations were made with the MVD assay, using three different δ-selective agonists ([Leu⁵]enkephalin, DPDPE and [D-Ala²]deltorphin I].

TABLE 1

IC50 values of cyclic β-casomorphin analogs in the GPI assay.
Prior known compounds are marked (P).

| Ex. | Compound | IC50 | [nM]* |
|---|---|---|---|
|  | H-Tyr-c[-D-Orn-2-Nal-D-Pro-Gly-] (P) | 384 | ±52 |
|  | H-Tyr-c[-D-Lys-2-Nal-D-Pro-Gly-] (P) | 609 | ±194 |
| 1 | Tyr(NMe)-c[-D-Orn-2-Nal-D-Pro-Gly-] | 92.5 | ±8.3 |
| 2 | H-Tyr-c[-D-Orn-2-Nal-D-Pro-Sar-] | 159 | ±24 |
| 3 | H-Dmt-c[-D-Orn-2-Nal-D-Pro-Gly-] | 7.88 | ±0.93 |
| 4 | H-Dmt-c[-D-Orn-2-Nal-D-Pro-Sar-] | 14.5 | ±1.6 |
| 5 | H-Tyr-c[-D-Orn-2-Nal-D-Pro-D-Ala-] | 600 | ±162 |
| 6 | H-Tyr-c[-D-Orn-2-Nal-D-Pro-Aib-] | 451 | ±110 |
| 7 | H-Tyr-c[-D-Orn-2-Nal-D-Pro-MeAib-] | 228 | ±21 |
| 8 | H-Tyr-c[-D-Orn-2-Nal-D-Pro-D-Val-] | 536 | ±34 |
| 9 | H-Tyr-c[-D-Orn-2-Nal-D-Pro-D-Ile-] | 815 | ±159 |
| 10 | H-Dmt-c[-D-Orn-2-Nal-D-Pro-D-Ala-] | 10.4 | ±1.8 |

*Values are means of 3–6 determinations ± SEM

TABLE 2

$K_e$ values of cyclic β-casomorphin analogs in the MVD assay (antagonist potencies against the δ agonists [Leu⁵]enkephalin, [D-Pen², D-Pen⁵]enkephalin (DPDPE) and [D-Ala²]deltorphin I.
Prior known compounds are marked (P).

| Ex. | Compound | [Leu⁵]-enkephalin | DPDPE | [D-Ala²]-deltorphin I |
|---|---|---|---|---|
|  | H-Tyr-c[-D-Orn-2-Nal-D-Pro-Gly-] (P) | 268 ± 22 | 233 ± 28 | 202 ± 24 |
|  | H-Tyr-c[-D-Lys-2-Nal-D-Pro-Gly-] (P) | 603 ± 174 | 305 ± 52 | 305 ± 52 |
| 1 | Tyr(NMe)-c[-D-Orn-2-Nal-D-Pro-Gly-] | 30.8 ± 1.5 | 45.9 ± 2.8 | 38.8 ± 5.9 |
| 2 | H-Tyr-c[-D-Orn-2-Nal-D-Pro-Sar-] | 17.0 ± 3.60 | 11.2 ± 2.1 | 7.81 ± 1.90 |
| 3 | H-Dmt-c[-D-Orn-2-Nal-D-Pro-Gly-] | 3.74 ± 1.00 | 2.13 ± 0.51 | 3.37 ± 0.59 |
| 4 | H-Dmt-c[-D-Orn-2-Nal-D-Pro-Sar-] | ND | 16.4 | ND |
| 5 | H-Tyr-c[-D-Orn-2-Nal-D-Pro-D-Ala-] | ND | 5.35 ± 0.42 | 5.99 ± 1.30 |
| 6 | H-Tyr-c[-D-Orn-2-Nal-D-Pro-Aib-] | ND | 31.6 ± 2.9 | 55.8 ± 3.8 |
| 7 | H-Tyr-c[-D-Orn-2-Nal-D-Pro-MeAib] | ND | 370 ± 48 | 480 ± 84 |
| 8 | H-Tyr-c[-D-Orn-2-Nal-D-Pro-D-Val-] | ND | 20.9 ± 1.5 | 26.1 ± 2.8 |
| 9 | H-Tyr-c[-D-Orn-2-Nal-D-Pro-D-Ile-] | ND | 4.88 ± 0.94 | 7.63 ± 1.48 |
| 10 | H-Dmt-c[-D-Orn-2-Nal-D-Pro-D-Ala-] | ND | 0.577 ± 0.022 | 0.319 ± 0.091 |

*Values are means of 3–8 determinations ± SEM

Conclusion

All compounds show mixed μ agonist/δ antagonist properties.

In comparison with the prior known compounds, the new analogs show greatly enhanced μ agonist potencies, and/or increased δ antagonist potencies.

Opioid receptor binding assays

μ and δ opioid receptor binding constants ($K_i^\mu$, $K_i^\delta$) of the compounds were determined by displacement of relatively selective μ- and δ-radioligands from binding sites in rat brain membrane preparations (calculated from the measured IC50 values on the basis of the equation by Cheng and Prusoff (Y. C. Cheng and W. H. Prusoff, (Biochem. Pharmacol. 22, 3099–3102 (1973)).

In the following Table 3 the results of opioid receptor binding assays are given. The ratio $K_i^\delta/K_i^\mu$ is a quantitative measure of the selectivity for μ versus δ receptors.

Opioid receptor binding studies

The μ-, δ- and κ-opioid receptor affinitives of all new analogs were determined in binding assays based on displacement of μ-, δ- and κ- selective radioligands from rat brain membrane binding sites. In the case of κ-ligands guinea pig brain homogenates were used, since the relative proportion of κ-binding sites is higher in guinea pig brain than in rat brain. The experimental procedure being used in our laboratory represents a modified version of the binding assay described by Paternak et al. (Mol. Pharmacol. 11 340–351, (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris-HCl, pH 7.7). After centrifugation at 30.000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [³H] DAMGO, μ-selective, 0.7 nM; [³H]DSLET, [³H]DPDPE, or [³H]TIPP, δ-selective, 1.0 nM; and [³H]U69,563, κ-selective, 0.5 nM. The incubation was terminated by filtration through Whatman GF/B filters under vacuum at 4° C. Following two washings with 5 ml portions of ice-cold standard buffer the filters were transferred to scintillation vials and treated with 1 ml Protosol (New England Nuclear) for 30 min prior to the addition of 0.5 ml acetic acid and 10 ml Aquasol (New England Nuclear). After shaking for 30 min the vials were counted at an efficiency of 40–45%. All experiments were performed in duplicates and repeated at least three times. Specific binding of each of the three radioglands was defmed by performing incubations in the presence of cold DAMGO, DSLET and U69,563, respectively, at a concentration of 1 micromolar. Values of half-maximal inhibition (IC50) of specific binding were obtained graphically from semilogarithmic plots. From the measured IC50-values, binding inhibition constants ($K_i$) were then calculated based on Cheng and Prussoff's equation (Biochem. Pharmacol. 22, 3099–3102 (1973)). Ratios of the $K_i$-values in the μ-, δ- and κ-representative bindning assays are a measure of the receptor selectivity of the compound under investigation (e.g. $K_i^\delta/K_i^\mu$ indicated the selectivity for μ-receptors versus δ-receptors). None of the compounds according to the claimed invention had significant affinity for κ-receptors.

TABLE 3

Receptor binding data of cyclic β-casomorphin analogs.
Prior known compounds are marked (P).

| Ex. | Compound | $K_i^\mu$ [nM]* | $K_i^\delta$ [nM]* | $K_i^\delta/K_i^\mu$ |
|---|---|---|---|---|
|  | H-Tyr-c[-D-Orn-2-Nal-D-Pro-Gly-] (P) | 5.89 ± 1.60 | 17.2 ± 4.9 | 2.92 |
|  | H-Tyr-c[-D-Lys-2-Nal-D-Pro-Gly-] (P) | 17.1 ± 2.6 | 62.6 ± 13.2 | 3.66 |
| 1 | Tyr(NMe)-c[-D-Orn-2-Nal-D-Pro-Gly-] | 1.70 ± 0.15 | 1.30 ± 0.19 | 0.765 |
| 2 | H-Tyr-c[-D-Orn-2-Nal-D-Pro-Sar-] | 14.8 ± 0.7 | 2.41 ± 0.34 | 0.163 |
| 3 | H-Dmt-c[-D-Orn-2-Nal-D-Pro-Gly-] | 0.460 ± 0.022 | 0.457 ± 0.022 | 0.993 |
| 5 | H-Tyr-c[-D-Orn-2-Nal-D-Pro-D-Ala-] | 72.0 ± 22.0 | 0.755 ± 0.125 | 0.0105 |
| 7 | H-Tyr-c[-D-Orn-2-Nal-D-Pro-MeAib] | 29.2 ± 5.2 | 10.7 ± 5.5 | 0.366 |

*Values are means of three determinations ± SEM.

Pontential use

On the basis of the results of a recent study performed by E. E. Abdelhamid et al., J. Pharmacol. Exp. Ther. 258, 299–303 (1991), the novel compounds with mixed μ agonist/δ antagonist properties should be therapeutically useful as analgesics that do not produce tolerance and dependence. In comparison with the TIPP-NH$_2$ and TIPP-NH$_2$ analogs with mixed μ agonist/δ antagonist properties, the mixed μ agonist/δ antagonists of the cyclic β-casomorphin type represent a structurally different class of compounds and may behave differently in in vivo situations in terms of bioavailability, stability and ability to cross the blood-brain barrier.

Abbreviations

Aib=α-aminoisobutyric acid
Boc=tert-butoxycarbonyl
Bzl=benzyl
DAMGO=H-Tyr-D-Ala-Gly-Phe(NMe)-Gly-ol
DIC=diisopropylcarbodiimide
DIPE=diisopropyl ether
DMAP=4-dimethylaminopyridine
Dmt=2',6'-dimethyltyrosine
DPDPE=[D-Pen$^2$, D-Pen$^5$]enkephalin
DPPA=diphenylphosphoryl azide
DSLET=H-Tyr-D-Ser-Gly-Phe-Leu-Thr-OH
FAB-MS=fast atom bombardment mass spectrometry
GPI=guinea pig ileum
HOBbt=1-hyroxybenzotriazole
IBCF=isobutylchloroformate
MVD=mouse vas deferens
Nal=naphthylalanine
NMM=N-methylmorpholine
ONb=p-nitrobenzyl ester
Orn=ornithine
PE=petroleum ether
PITC=phenylisothiocyanate
RP-HPLC=reversed-phase high performance liquid chromatography
Sar=sarcosine
tBu=tert.-butyl
TFA=trifluoroacetic acid
Tic=1,2,3,4-tetrahydroisoquinoine-3-carboxylic acid
TIPP-NH$_2$=H-Tyr-Tic-Phe-Phe-NH$_2$
TLC- thin layer chromatography
Tyr(NMe)=N$^\alpha$-methyltyrosine
U69,593=(5α,7α,8β)-(−)-N-methyl-[7-(1-pyrrolidinyl)-1-oxaspiro[4,5]dec-8-yl]benzene-acetamnide
Z=benzyloxycarbonyl

We claim:

1. A compound of the formula (I)

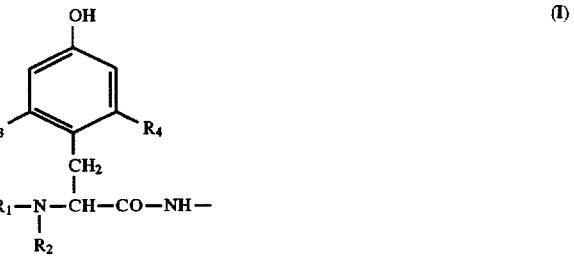

(I)

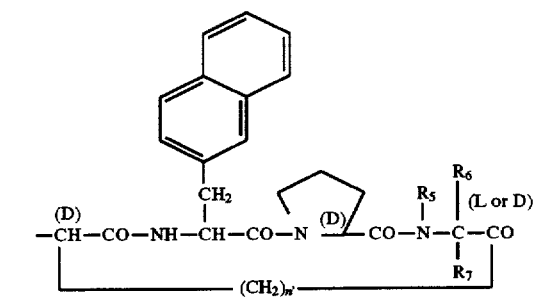

n' = 1–6 wherein $R_1$ is H, or CH$_3$(CH$_2$)$_{n^2}$—, wherein n$^2$ = 0–12, or

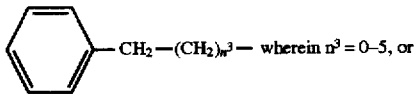

—CH$_2$—(CH$_2$)$_{n^3}$— wherein n$^3$ = 0–5, or

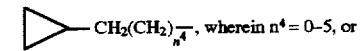

—CH$_2$(CH$_2$)$_{\overline{n^4}}$, wherein n$^4$ = 0–5, or

CH$_2$ = CH—CH$_2$—, or arginine; R$_2$ is H, or CH$_3$(CH$_2$)$_{n^2}$— wherein n$^2$ = 0–12, or ▷—CH$_2$— or CH$_2$=CH—CH$_2$—;

R$_3$ and R$_4$ respectively, are both H or are both C$_1$–C$_6$ alkyl groups;

R$_5$ is H or a C$_1$–C$_6$ alkyl group;

R$_6$ is H or a C$_1$–C$_6$ alkyl group;

R$_7$ is H or a C$_1$–C$_6$ alkyl group;

with the exceptions of compounds wherein R$_1$, R$_2$, R$_3$, R$_4$, R$_5$, R$_6$ and R$_7$ are all H, and the number (n') of methylene groups in the 2-position side chain is 2,3 or 4.

2. A compound according to formula I of claim 1, wherein R$_3$, R$_4$, R$_6$ and R$_7$ are the same or different and each is a C$_1$–C$_4$ alkyl group.

3. A compound according to formula I of claim 1, wherein R$_1$ is selected from the group consisting of:

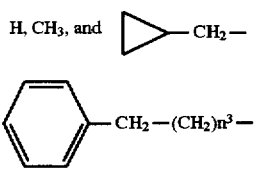

$R_2$ is hydrogen;

$R_3$ and $R_4$ are each a $CH_3$ group;

$R_5$ is hydrogen;

$R_6$ is $CH_3$; and $R_7$ is hydrogen.

4. A compound according to formula I of claim 1, wherein $R_3$ and $R_4$ are both methyl groups.

5. A compound according to formula I of claim 1, wherein $R_5$ is a methyl group and $R_6$ and $R_7$ are both hydrogen.

6. A compound according to formula I of claim 1, wherein $R_1$ is a methyl group and $R_2$ is hydrogen.

7. A compound according to formula I of claim 1, wherein $R_5$ and $R_6$ are hydrogen, $R_7$ is a methyl group and the configuration of the fifth amino acid residue (alanine) is D.

8. A compound according to formula I of claim 1, wherein $R_5$ is hydrogen and $R_6$ and $R_7$ are both methyl groups.

9. A compound according to claim 1, wherein said compound is selected from the group consisting of:

Tyr-(NMe.)-c[-D-Orn-2-Nal-D-Pro-Gly-];

H-Tyr-c[-D-Orn-2-Nal-D-Pro-Sar-];

H-Dmt-c[-D-Orn-2-Nal-D-Pro-Gly-];

H-Dmt-c[-D-Orn-2-Nal-D-Pro-Sar-];

H-Tyr-c[-D-Orn-2-Nal-D-Pro-D-Ala-];

H-Tyr-c[-D-Orn-2-Nal-D-Pro-Aib];

H-Tyr-c[-D-Orn-2-Nal-D-Pro-MeAib-];

H-Tyr-c[-D-Orn-2-Nal-D-Pro-D-Val-];

H-Tyr-c[-D-Orn-2-Nal-D-Pro-D-Ile-]; and

H-Dmt-[-D-Orn-2-Nal-D-Pro-D-Ala-].

10. A compound according to claim 1, wherein said compound is selected from the group consisting of:

H-Dmt-c[-D-Orn-2-Nal-D-Pro-Gly-]; and

H-Dmt-[-D-Orn2-Nal-D-Pro-D-Ala-].

11. A method for preparing a compound according to claim 1 in solution employing mixed anhydrides, wherein:

(a) a linear pentapeptide precursor is built up in a stepwise fashion starting at the C-terminus; and (b) cyclization between the ω-amino group of the 2-position residue and the c-terminal carboxyl group is performed in dilute solution with diphenylphosphoryl azide as a coupling agent.

12. A method for preparing a compound according to claim 1 by solid-phase synthesis, wherein:

(a) a linear pentapeptide is assembled on a resin using a super acid-sensitive dialkoxybenzyl alcohol linker and Fmoc-amino acids; and (b) after cleavage from said resin and deprotection of the ω-amino group of the 2-position residue, said compound is cyclized in dilute solution using diphenylphosphoryl azide as a coupling agent.

13. A pharmaceutical composition comprising a compound according to claim 1 together with one or more pharmaceutically acceptable carriers.

14. A method for the treatment of pain in a subject in need of such-treatment, comprising:

administering a compound according to claim 1 to said subject wherein said compound is administered in an amount effective to reduce or eliminate said pain.

* * * * *